(12) United States Patent
Okazaki (10) Patent No.: US 8,758,603 B2
(45) Date of Patent: Jun. 24, 2014

(54) PLASMA PURIFYING DEVICE AND METHOD OF CONTROLLING PLASMA PURIFYING DEVICE

(75) Inventor: Soichiro Okazaki, Tokyo (JP)

(73) Assignee: Asahi Kasei Medical Co., Ltd., Tokyo (JP)

(*) Notice: Subject to any disclaimer, the term of this patent is extended or adjusted under 35 U.S.C. 154(b) by 628 days.

(21) Appl. No.: 13/129,703

(22) PCT Filed: Nov. 19, 2009

(86) PCT No.: PCT/JP2009/006235
§ 371 (c)(1),
(2), (4) Date: Aug. 8, 2011

(87) PCT Pub. No.: WO2010/058583
PCT Pub. Date: May 27, 2010

(65) Prior Publication Data
US 2011/0284467 A1 Nov. 24, 2011

(30) Foreign Application Priority Data
Nov. 19, 2008 (JP) ................. 2008-295719

(51) Int. Cl.
*B01D 21/24* (2006.01)
*B01D 24/38* (2006.01)
*A61M 1/34* (2006.01)

(52) U.S. Cl.
CPC ........... *A61M 1/3472* (2013.01); *A61M 1/3496* (2013.01)
USPC ............. 210/97; 210/660; 210/645; 210/650; 210/741; 210/108; 210/111

(58) Field of Classification Search
CPC ............ A61M 1/3472; A61M 1/3643; A61M 2001/3646; A61M 2001/365; A61M 2001/3652
USPC .................................................. 210/97, 660
See application file for complete search history.

(56) References Cited

U.S. PATENT DOCUMENTS 5,314,624 A 5/1994 Kawakura et al.
6,083,187 A 7/2000 Nakayama et al.

FOREIGN PATENT DOCUMENTS

| CN | 2689953 | 4/2005 |
|---|---|---|
| CN | 101062433 | 10/2007 |
| EP | 0 181 139 | 5/1986 |
| JP | 61-113457 | 5/1986 |

(Continued)

OTHER PUBLICATIONS

International Preliminary Report on Patentability for PCT/JP2009/006235, mailed Jun. 30, 2011.

(Continued)

*Primary Examiner* — Dirk Bass
(74) *Attorney, Agent, or Firm* — Greenblum & Bernstein P.L.C.

(57) ABSTRACT

A plasma purifying device is provided that is capable of recovering blood and plasma remaining within the plasma purifying device easily and without risk of coagulation, following completion of plasma purification therapy. The plasma purifying device has a control unit controls flow rates of the air pump and a plasma pump so that a pressure of the filtration side space of the plasma separator is higher than a pressure of the blood side space while delivering blood to the blood side space of the plasma separator by continuing to operate a blood pump without stopping following completion of plasma purification and then delivers plasma remaining in a filtration side space of a plasma separator to a blood side space of the plasma separator or to a plasma circuit by supplying air from an air pump.

9 Claims, 3 Drawing Sheets

(56) References Cited

FOREIGN PATENT DOCUMENTS

| | | |
|---|---|---|
| JP | 62-281956 | 12/1987 |
| JP | 64-5563 | 1/1989 |
| JP | 1-17704 | 3/1989 |
| JP | 2-177962 | 7/1990 |
| JP | 5-38362 | 2/1993 |
| JP | 7-88179 | 4/1995 |
| JP | 10-80478 | 3/1998 |
| JP | 2001-54571 | 2/2001 |
| WO | 92/17220 | 10/1992 |

OTHER PUBLICATIONS

Chinese Official Action, mail date is Jun. 20, 2013.
International Preliminary Report on Patentability for PCT/JP2009/006235, mailed Jun. 21, 2011.

PLASMA PURIFYING DEVICE AND METHOD OF CONTROLLING PLASMA PURIFYING DEVICE

TECHNICAL FIELD

The present invention relates to a plasma purifying device and a method of controlling a plasma purifying device.

BACKGROUND ART

Plasma purifying devices that carry out plasma purification therapy such as separation of plasma components of plasma adsorption have a collected blood circuit, a return blood circuit, a plasma circuit, a plasma separator and a plasma component separator or plasma adsorber. Following completion of plasma component separation or plasma adsorption, blood remains in the collected blood circuit, the return blood circuit and blood side space of the plasma separator, and plasma remains in the filtration side space of the plasma separator, the plasma circuit, and the plasma component separator or plasma adsorber. Since the blood and plasma remaining in the above-mentioned circuits, the plasma separator and the plasma component separator or plasma adsorber are useful components, they are typically returned to the patient following plasma purification therapy. However, since plasma purification therapy uses not only a plasma separator, but also a plasma component separator or plasma adsorber, the overall device is complex and requires an extremely complex operation such as adjusting flow rates, driving and stopping of a blood pump and plasma pump, or opening and closing blood circuits and plasma circuits using Pean hemostatic forceps and the like. Therefore, methods for easily recovering blood and plasma have been proposed as in Patent Document 1 and Patent Document 2. Both of these publications disclose a method for automatically recovering blood and plasma by switching the operations of various valves and pumps using pressure and cumulative operating amounts of pumps.

Figure 3:
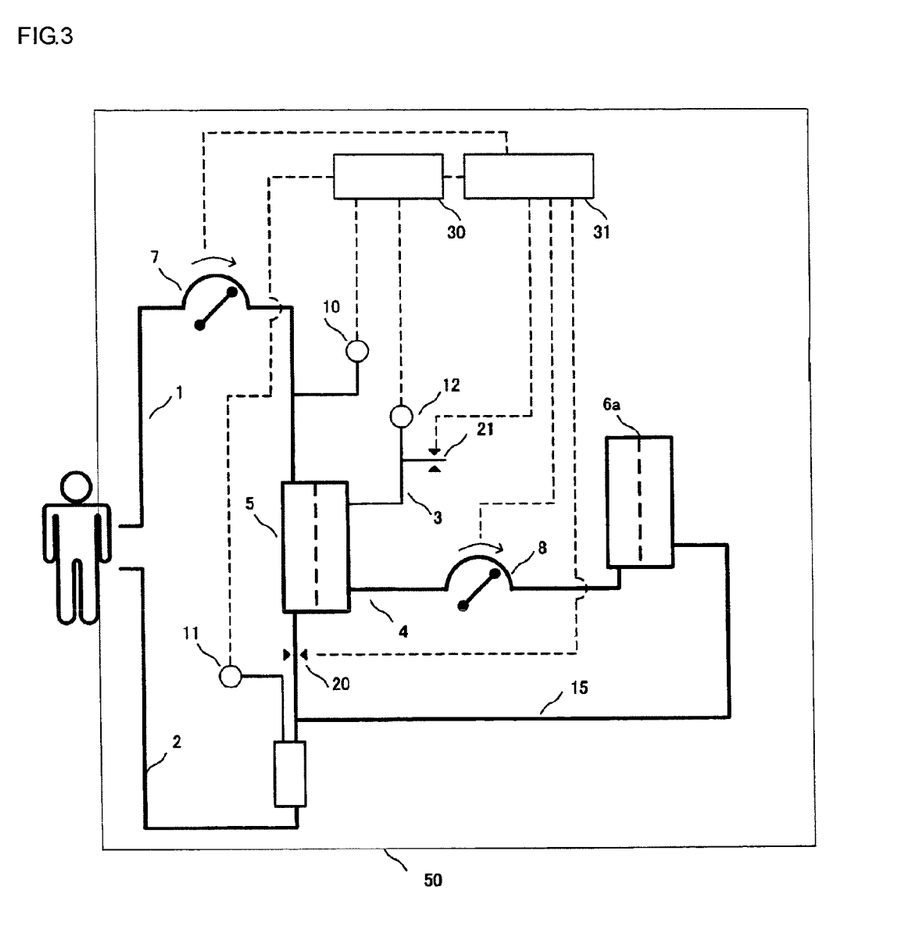

FIG. 3 shows an example of the configuration of a plasma component separation device 50 as an embodiment of Patent Document 1.

The plasma component separation device 50 has a plasma separator 5 and a plasma component separator 6a. A collected blood circuit 1 is connected to a blood inlet of the plasma separator 5, and a blood pump 7 is arranged in the collected blood circuit 1. First pressure measuring means 10 is arranged between the blood pump 7 and the plasma separator 5. A return blood circuit 2 is connected to the blood outlet of the plasma separator 5, and second pressure measuring means 11 is arranged in the return blood circuit 2. A first pressure measurement circuit 3 is connected to a first filtration outlet of the plasma separator 5, a plasma circuit 4 is connected to a second filtration outlet, the plasma circuit 4 is connected to the plasma component separator 6a, and a blood pump 8 is arranged in the plasma circuit 4. Third pressure measuring means 12 and a branch line are arranged in the first pressure measurement circuit 3, and a second valve 21 is arranged in the branch line. A return plasma circuit 15 is connected to a first plasma component outlet of the plasma component separator 6a. The return plasma circuit 15 is connected to the return blood circuit 2, and a first valve 20 is arranged upstream from the junction of the return plasma circuit 15 and the return blood circuit 2. The plasma component separation device 50 further has an arithmetic processing unit 30 and a control unit 31. The arithmetic processing unit 30 and the control unit 31 are connected, and arithmetic processing unit 30 is connected to the first pressure measuring means 10, the second pressure measuring means 11, and the third pressure measuring means 12, while the control unit 31 is connected to the blood pump 7, the plasma pump 8, the first valve 20 and the second valve 21.

The above provides a description of the overall configuration of the blood component separation device 50 of Patent Document 1. Next, an explanation is provided of the operating method of the plasma component separation device 50 for recovering blood and plasma following completion of plasma purification therapy.

In the state following completion of plasma purification, the collected blood circuit 1, the return blood circuit 2 and the blood side space of the plasma separator 5 are filled with blood. In addition, the filtration side space of the plasma separator 5, the plasma circuit 4, the plasma component separator 6a and the return plasma circuit 15 are filled with plasma. At this time, since the collected blood circuit 1 and the return blood circuit 2 are still connected to the patient, and the blood pump 7 is still operating, the blood pump 7 is temporarily stopped, and the collected blood circuit 1 is disconnected from the patient and connected to physiological saline for recovery.

Once the collected blood circuit 1 has been connected to the physiological saline for recovery, operation of the blood pump 7 is resumed and blood is recovered from the collected blood circuit 1, the plasma separator 5 and the return blood circuit 2. At this time, since the plasma pump 8 is stopped with the filtration side space of the plasma separator 5, the plasma circuit 4, the plasma component separator 6a and the return plasma circuit 15 still filled with plasma, there is the risk of the plasma coagulating if an excessive amount of time is required to recover the blood.

Next, the blood pump 7 is stopped, the first valve 20 is closed, the second valve 21 is opened and the plasma pump 8 is operated to recover plasma from the filtration side space of the plasma separator 5, the plasma circuit 4, the plasma component separator 6a and the return plasma circuit 15. Since the blood pump 7 is stopped at this time, there is the risk of blood coagulation is blood has not been recovered as previously described. Once recovery of plasma has been completed, the return blood circuit is disconnected from the patient.

As has been described above, in this recovery method, since the plasma pump 8 is stopped during recovery of blood, clogging may occur in the plasma component separator 6a or a plasma adsorber 6b thereby preventing subsequent recovery of plasma even if the plasma pump 8 is operated. In addition, even if plasma is recovered first followed by recovery of blood, since the blood pump 7 is stopped during recovery of plasma, there is the risk of blood coagulating in the collected blood circuit 1, the return blood circuit 2 and the blood side space of the plasma separator 5.

Moreover, during recovery of blood, there is the disadvantage of handling of work having to be performed by two people consisting of a person who handles the patient after disconnecting the collected blood circuit or return blood circuit from the site where connected to the patient, and a person who handles the plasma purifying device. Namely, work performed by two persons begins when the collected blood circuit is disconnected from the patient, and ends when all recovery work has been completed and the return blood path is disconnected from the patient.

Since the flow rate of a blood pump is typically about 100 mL/min, and the amount of blood remaining in the collected blood circuit, the return blood circuit and the blood side space of the plasma separator is about 200 mL, blood recovery is completed in about 2 minutes. On the other hand, since the plasma component separator or plasma adsorber can become clogged if the flow rate of the plasma pump is excessively high, it is typically amount 20 mL/min. Since amount 200 mL of plasma remain in the filtration side space of the plasma separator, the plasma circuit and the plasma component separator or plasma adsorber, it ends up taking about 10 minutes to recover plasma. Consequently, this results in the disadvantage of prolonging the amount of time required for the work performed by two persons.

CITATION LIST

Patent Literature

[Patent Document 1] Japanese Examined Patent Publication No. H1-17704
[Patent Document 2] Japanese Patent Application Laid-open No. 2001-54571

SUMMARY OF INVENTION

Technical Problem

With the foregoing in view, an object of the present invention is to provide a plasma purifying device capable of easily and without risk of coagulation recovering blood and plasma remaining within the plasma purifying device following completion of plasma purification therapy.

Solution to Problem

As a result of conducting extensive studies to solve the above-mentioned problems, the inventors of the present invention found that plasma remaining in a filtration side space of a plasma separator can be recovered by taking advantage of the characteristic of a filtration membrane such as a hollow fiber, namely that air is unable to pass there through once wetted with a liquid such as blood or physiological saline, thereby leading to completion of the present invention. Namely, the present invention relates to the following:

(i) a plasma purifying device comprising: a plasma separator for which a collected blood circuit is connected to a blood inlet, a return blood circuit is connected to a blood outlet, a first pressure measurement circuit is connected to a first filtration outlet and a plasma circuit is connected to a second filtration outlet; a plasma component separator or plasma adsorber for which the plasma circuit is connected to a plasma inlet, and a plasma circuit leading to the return blood circuit is connected to a plasma outlet, a blood pump which is installed in the collected blood circuit, and which supplies blood to a blood side space of the plasma separator; a plasma pump which is installed in the plasma circuit, and which supplies plasma to the plasma component separator or the plasma adsorber; an air pump which is installed in the first pressure measurement circuit, and which supplies air to a filtration side space of the plasma separator; and a control unit for controlling flow rates of the air pump and the plasma pump so that a pressure of the filtration side space of the plasma separator is higher than a pressure of the blood side space while delivering blood to the blood side space of the plasma separator by continuing to operate the blood pump without stopping following completion of plasma purification, and then delivering plasma remaining in the filtration side space of the plasma separator to the blood side space of the plasma separator or to the plasma circuit by supplying air from the air pump;

(ii) the plasma purifying device described in (i), wherein the control unit delivers the plasma within the plasma circuit to the plasma component separator or the plasma adsorber by controlling the flow rates of the plasma pump and the air pump so that a difference between a pressure of the blood side space and a higher pressure of the filtration side space is not more than a preset reference value while continuing to operate the blood pump after plasma within the filtration side space of the plasma separator has been replaced with air;

(iii) the plasma purifying device described in (ii), wherein the plasma purifying device further has first pressure measuring means for measuring a pressure $P1$ of the collected blood circuit, second pressure measuring means for measuring a pressure $P2$ of the return blood circuit, third pressure measuring means for measuring a pressure $P3$ of the first pressure measurement circuit, and an arithmetic processing unit for calculating, from the pressures $P1$, $P2$ and $P3$, a trans-membrane pressure difference TMP defined by either of the following formulas (1) and (2), and the control unit delivers the plasma within the plasma circuit to the plasma component separator or the plasma adsorber by controlling the flow rates of the plasma pump and the air pump so that the trans-membrane pressure difference TMP is within a prescribed negative pressure range:

$$(P1+P2)/2-P3=TMP \quad (1)$$

$$P1-P3=TMP \quad (2);$$

(iv) the plasma purifying device described in (iii), wherein the control unit adjusts the flow rate of the air pump so as to be greater than the flow rate of the plasma pump in a case where the trans-membrane pressure difference TMP is equal to or greater than an upper limit value of the prescribed negative pressure range, and operates the plasma pump while stopping the air pump in a case where the trans-membrane differential pressure TMP is equal to or less than the lower limit value of the prescribed negative pressure range;

(v) the plasma purifying device described in (iii) or (iv), wherein the prescribed negative pressure range of the TMP is from −100 mmHg to −10 mmHg;

(vi) the plasma purifying device described in any of (i) to (v), wherein the plasma purifying device has a plasma component separator, has fourth pressure measuring means for measuring a pressure $P4$ of the plasma circuit between the plasma pump and the plasma component separator, a branch circuit connected to a first plasma component outlet of the filtration side space of the plasma component separator, and a return plasma pump installed in the branch circuit, the return plasma circuit connects a second plasma component outlet of the filtration side space of the plasma component separator with the return blood circuit, the arithmetic processing unit calculates a pressure difference ΔP defined by the following formula (3) from the pressures $P3$ and $P4$, and the control unit delivers the plasma of the filtration side space of the plasma component separator and plasma of the return plasma circuit to the return blood circuit by stopping the plasma pump and the air pump and operating the return plasma pump while continuing to operate the blood pump when the pressure difference ΔP is equal to or greater than a reference value within a prescribed pressure range:

$$P4-P3=\Delta P \quad (3);$$

(vii) the plasma purifying device described in (vi), wherein the prescribed pressure range of the ΔP is from 200 mmHg to 500 mmHg;

(viii) the plasma purifying device described in any of (i) to (vii), wherein the control unit delivers the plasma of the filtration side space of the plasma separator to the blood side space of the plasma separator by operating the air pump and stopping the plasma pump;

(ix) a plasma purifying device comprising: a plasma separator for which a collected blood circuit is connected to a blood inlet, a return blood circuit is connected to a blood outlet, a first pressure measurement circuit is connected to a first filtration outlet, and a plasma circuit is connected to a second filtration outlet; a plasma component separator or a plasma adsorber for which the plasma circuit is connected to a plasma inlet and a return plasma circuit leading to the return blood circuit is connected to a plasma outlet; a blood pump which is installed in the collected blood circuit, and which supplies blood to a blood side space of the plasma separator; a plasma pump which is installed in the plasma circuit, and which supplies plasma to the plasma component separator or the plasma adsorber; an air pump which is installed in the first pressure measurement circuit, and which supplies air to a filtration side space of the plasma separator; and a control unit for controlling flow rates of the blood pump, the plasma pump and the air pump, wherein the control unit controls the flow rates of the air pump and the plasma pump while delivering blood to the blood side space of the plasma separator by operating the blood pump and delivers plasma remaining in the filtration side space to the blood side space and the plasma circuit by supplying air to the filtration side space of the plasma separator, and also controls the flow rates of the air pump and the plasma pump and delivers plasma remaining in the plasma circuit to the plasma component separator or the plasma adsorber; and (x) a method of controlling a plasma purifying device, the method comprising: a step of delivering plasma remaining in a filtration side space of a plasma separator to a blood side space of the plasma separator and to a plasma circuit by supplying air to the filtration side space of the plasma separator while delivering blood to the blood side space of the plasma separator by operating a blood pump; and a step of delivering plasma remaining in a plasma circuit to a plasma component separator or a plasma adsorber by supplying air to the plasma circuit.

Advantageous Effects of Invention

According to the present invention, since plasma remaining in a filtration side space of a plasma separator, a plasma circuit and a plasma component separator or plasma adsorber can be continuously recovered while continuing to operate a blood pump, the risk of coagulation of the blood and plasma is eliminated. In addition, since plasma can be recovered without disconnecting a collected blood circuit from a patient, plasma recovery work is not required to be performed by two persons, thereby dramatically improving the efficiency of plasma recovery work.

DESCRIPTION OF EMBODIMENTS

Figure 1:
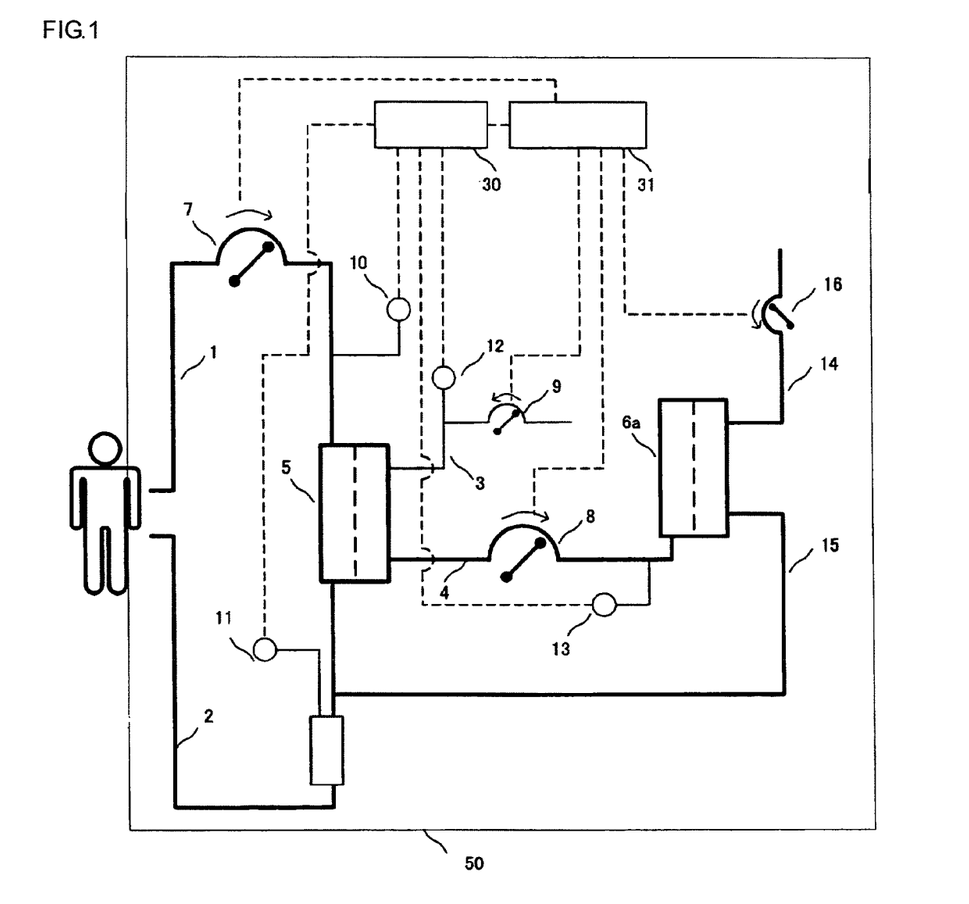
FIG. 1 is an explanatory drawing of a plasma component separation device according to the present invention.

The following provides a detailed explanation of the present invention using the appended drawings. FIG. 1 shows an example of the configuration of a plasma component separation device (plasma purifying device) 50 as one embodiment of the present invention.

The plasma component separation device 50 has a plasma separator 5 and a plasma component separator 6a. A collected blood circuit 1 is connected to a blood inlet of the plasma separator 5, and a blood pump 7 is arranged in the collected blood circuit 1. First pressure measuring means 10 is arranged between the blood pump 7 and the plasma separator 5. A return blood circuit 2 is connected to the blood outlet of the plasma separator 5, and second pressure measuring means 11 is arranged in the return blood circuit 2. A first pressure measurement circuit 3 is connected to a first filtration outlet of the plasma separator 5, a plasma circuit 4 is connected to a second filtration outlet, the plasma circuit 4 is connected to the plasma component separator 6a, and a blood pump 8 is arranged in the plasma circuit 4. Third pressure measuring means 12 and a branch line are arranged in the first pressure measurement circuit 3, and an air pump 9 is arranged in the branch line. A branch circuit 14 is connected to a first plasma component outlet of a filtration side space of the plasma component separator 6a, and a return plasma circuit 15 is connected to a second plasma component outlet. A return plasma pump 16 is arranged in the branch circuit 14, and the return plasma circuit 15 is connected to the return blood circuit 2. The plasma component separation device 50 further has arithmetic processing unit 30 and control unit 31. The arithmetic processing unit 30 and the control unit 31 are connected, the arithmetic processing unit 30 is connected to the first pressure measuring means 10, the second pressure measuring means 11, the third pressure measuring means 12 and fourth pressure measuring means 13, and the control unit 31 is connected to the blood pump 7, the plasma pump 8, the air pump 9 and the return plasma pump 16.

The arithmetic processing unit 30 calculates a trans-membrane differential pressure TMP defined by either of the following formulas (1) and (2) from a pressure P1 of the collected blood circuit 1 measured by the first pressure measuring means 10, a pressure P2 of the return blood circuit 2 measured by the second pressure measuring means 11, and a pressure P3 of the first pressure measurement circuit 3 measured by the third pressure measuring means 12.

$$(P1+P2)/2-P3=TMP \quad (1)$$

$$P1-P3=TMP \quad (2)$$

In addition, the control unit 31 is able to deliver plasma remaining in the filtration side space of the plasma separator 5 to the blood side space of the plasma separator 5 or the plasma circuit 4 by supplying air from the air pump 9 by controlling the flow rates of the air pump 9 and the plasma pump 8 so that the pressure of the filtration side space of the plasma separator 5 is higher than the pressure of the blood side space while delivering blood to the blood side space of the plasma separator 5 by continuing to operate the blood pump 7 without stopping following completion of plasma purification.

In addition, the control unit 31 is able to deliver plasma within the plasma circuit 4 to the plasma component separator 6a by controlling the flow rates of the plasma pump 7 and the air pump 9 so that the difference between the pressure of the blood side space and the pressure of the higher filtration side space is equal to or less than a preset reference value while continuing to operate the blood pump 7 after plasma within the filtration side space of the plasma separator 5 has been replaced with air. More specifically, the control unit 31 is able to deliver plasma within the plasma circuit 4 to the plasma component separator 6a by controlling the flow rates of the plasma pump 7 and the air pump 9 so that the previously described trans-membrane pressure difference TMP is within a prescribed negative pressure range.

Moreover, the control unit 31 is able to deliver plasma of the filtration side space of the plasma component separator 6a and plasma of the plasma circuit 15 to the return blood circuit 2 by stopping the plasma pump 8 and the air pump 9 and operating the return plasma pump 16 while continuing to operate the blood pump 7 when a pressure difference ΔP (P4−P3) between the pressure P4 measured with the fourth pressure measuring means 13 and the pressure P3 measured with the third pressure measuring means 12 is equal to or greater than a certain reference value within a prescribed pressure range.

Furthermore, a computer, for example, can be used for the arithmetic processing unit 30 and the control unit 31, the functions described above can be realized by executing a program preliminarily recorded in memory.

The above has provided a description of the overall configuration of the plasma component separation device 50 of the present invention. Next, an explanation is provided of an operating method and control method of the plasma component separation device 50 that recovers blood and plasma following completion of plasma purification.

In the state in which plasma purification has been completed, the collected blood circuit 1, the return blood circuit 2 and the blood side space of the plasma separator 5 are filled with blood. In addition, the filtration side space of the plasma separator 5, the plasma circuit 4, the plasma component separator 6a and the return plasma circuit 15 are filled with plasma. At this time, the collected blood circuit and the return blood circuit are still connected to the patient, and the blood pump 7 and the plasma pump 8 are still operating.

Following completion of plasma purification, plasma is first recovered. In the initial stage of plasma recovery, plasma in the filtration side space of the plasma separator 5 is recovered by delivering to the blood side space of the plasma separator 5 of to the plasma circuit 4. Plasma delivered to the blood side space is recovered in the return blood circuit 2 directly, while plasma delivered to the plasma circuit 4 is recovered in the return blood circuit 2 after passing through the plasma circuit 4, the plasma component separator 6a and the return plasma circuit 15 as a general rule. At this time, the blood pump 7 is still operating, and blood in the collected blood circuit 1, the blood side space of the plasma separator 5 and the return blood circuit 2 is circulating. The flow rates of the air pump 9 and the plasma pump 8 are controlled so that the pressure of the filtration side space of the plasma separator 5 is higher than the pressure of the blood side space by operating the air pump 9 while still operating the plasma pump 8. More specifically, the flow rates are adjusted so that the flow rate of the air pump 9 is greater than the flow rate of the plasma pump 8. Since the pressure of the filtration side space of the plasma separator 5 becomes higher than the pressure of the blood side space by sending air to the filtration side space with the air pump 9, there is no additional separation of plasma from the blood in the plasma separator 5. The amount of air in the filtration side space of the plasma separator 5 gradually increases, and the filtration side space of the plasma separator 5 is ultimately replaced with air. Furthermore, the plasma pump 8 may be stopped in the case of desiring to not promote clogging of the plasma component separator 6a.

When air is further sent with the air pump 9 after having replaced the filtration side space of the plasma separator 5 with air, since a filtration membrane such as a hollow fiber that has been wetted has the property of not allowing the passage of air, the air that has been sent with the air pump 9 is compressed in the filtration side space of the plasma separator 5, the pressure P3 rises and the trans-membrane pressure difference TMP reaches negative pressure. At the point the trans-membrane pressure difference TMP becomes equal to or less than a certain reference value within a prescribed negative pressure range, recovery of plasma in the filtration side space of the plasma separator 5 ends. At this time, all of the plasma in the filtration side space of the plasma separator 5 is recovered into the blood side space of the plasma separator 5 or into the plasma circuit 4.

Next, plasma in the plasma circuit 4 is recovered. At this time, the blood pump 7 is still operating and blood is still circulating. In addition, plasma in the plasma circuit 4 is delivered to the plasma component separator 6a by controlling the flow rates of the air pump 9 and the plasma pump 8 so that the trans-membrane pressure difference TMP is within a prescribed negative pressure range. As a result, since the difference in pressure between the pressure of the blood side space and the higher pressure of the filtration side space can be adjusted to be equal to or less than a preset reference value (here, an absolute value of the lower limit of the prescribed negative pressure range), an excessive load can be prevented from acting on a separation membrane of the plasma separator 5 as a result of the value of the trans-membrane pressure difference TMP being excessively low (pressure difference being excessively large) and causing a large amount of plasma in the filtration side space to attempt to flow into the blood side space. Conversely, additional plasma can be prevented from flowing into the filtration side space from the blood side space of the plasma separator 5 as a result of the trans-membrane pressure difference TMP being excessively high (pressure difference being excessively small). Furthermore, although there are no particular limitations on the negative pressure range of the trans-membrane pressure difference TMP, in consideration of measuring accuracy of the pressure measuring means and suitable internal pressure in the circuits, the prescribed negative pressure range is preferably −100 mmHg (−13.3 kPa) to −10 mmHg (−1.3 kPa). More preferably, the prescribed negative pressure range is −80 mmHg (−10.6 kPa) to −20 mmHg (−2.6 kPa).

For example, in the case the trans-membrane pressure difference TMP has become equal to or greater than the upper limit value of the prescribed negative pressure range, the flow rate of the air pump 9 is adjusted to be greater than the flow rate of the plasma pump 8, while in the case the trans-membrane pressure difference TMP has become equal to or less than the lower limit value of the prescribed negative pressure range, the air pump 9 is stopped and the plasma pump 8 is operated. In addition, although either the flow rate of the air pump 9 or the flow rate of the plasma pump 8 may be varied provided the trans-membrane pressure difference TMP is within the prescribed negative pressure range, it is preferable to vary the flow rate of the air pump 9 while keeping the flow rate of the plasma pump 8 constant since it is preferable to maintain a constant flow rate when returning to the patient. Moreover, on/off control is preferably used to control on/off switching of the air pump 9 since this is advantageous in terms of cost. Although either formula (1) or formula (2) may be selected for the formula used to calculate TMP as previously described, formula (1) is preferable for preventing plasma from being separated in all regions from the inlet to the outlet of the plasma separator 5. Formula (2) may also be used without any particular problems if the prescribed negative pressure range is determined in consideration of the flow rate of the blood pump 7 and flow resistance such as membrane surface area of the plasma separator 5.

Once the plasma circuit 4 has been replaced with air and air has entered the inlet side of the plasma component separator 6a, since recovery of nearly all residual plasma is completed in the case the volume of the return plasma circuit 15 is small, recovery of plasma may be terminated at this time.

In addition, when the pressure difference ΔP (P4−P3) between the pressure P4 measured with the fourth pressure measuring means 13 and the pressure P3 measured with the third pressure measuring means 12 has gradually increased reached a value equal to or greater than a reference value within a prescribed pressure range, the plasma pump 8 and the air pump 9 are stopped and operation of the return plasma pump 16 is started while continuing to operate the blood pump 7, and plasma present in the return plasma circuit 15 and the filtration side space of the plasma component separator 6a at this time is recovered by delivering to the return blood circuit 2. As a result, plasma present on the side of the return blood circuit 2 can be suitably recovered with the separation membrane of the plasma component separator 6a while preventing an excessive rise in the pressure difference ΔP causing clogging and so on of the separation membrane of the plasma component separator 6a. Furthermore, the prescribed pressure range of ΔP is preferably 500 mmHg (66.6 kPa) or less in consideration of such factors as withstand pressure, and is preferably 200 mmHg (26 kPa) or less and in consideration of such factors as clogging of the plasma component separator 6a during completion of plasma purification. This step may be terminated while being visually confirmed by an operator, or may be terminated automatically at the time the return plasma pump 16 has operated for a prescribed amount from the volume of the return plasma circuit 15 and the filtration side space of the plasma component separator 6a.

Next, blood is recovered. At this time, the blood pump 7 is temporarily stopped, and the collected blood circuit 1 is connected to physiological saline for recovery. The duration of stoppage of the blood pump 7 is 1 minute or less, thereby eliminating the risk of coagulation of blood.

Once the collected blood circuit 1 has been connected to the physiological saline for recovery, operation of the blood pump 7 is resumed and blood is recovered from the collected blood circuit 1, plasma separator 5 and the return blood circuit 2. Although the plasma pump 8 is stopped at this time, since recovery of plasma has already been completed, there is no risk of coagulation of the plasma.

The procedure used to recover blood and plasma and examples of the operating states of the blood pump 7, the plasma pump 8, the air pump 9 and the return plasma pump 16 are summarized in Table 1.

TABLE 1

| | Ending conditions | Blood pump 7 | Plasma pump 8 | Air pump 9 | Return plasma pump 16 |
|---|---|---|---|---|---|
| 1 | Recovery of plasma from filtration side space of plasma separator | TMP ≤ reference value within prescribed negative pressure range | ON | OFF to ON | ON Controlled so that flow rate of air pump is greater than flow rate of plasma pump | OFF |
| 2 | Recovery of plasma from plasma circuit | ΔP ≥ reference value within prescribed pressure range | ON | ON | ON Controlled so that TMP reaches negative pressure | OFF |
| 3 | Recovery of plasma from return plasma circuit | Visual confirmation or prescribed amount of operation | ON | OFF | OFF | ON |
| 4 | Disconnection of collected blood circuit from patient and connection of collected blood circuit to physiological saline for recovery | Visual confirmation | OFF | OFF | OFF | OFF |
| 5 | Recovery of blood from collected blood circuit, plasma separator and return blood circuit | Visual confirmation or prescribed amount of operation | ON | OFF | OFF | OFF |

As has been described above, since plasma can be recovered without stopping the blood pump 7 and recovery of plasma can be completed prior to recovery of blood, the potential for coagulation of blood and plasma can be significantly reduced. In addition, by disconnecting the collected blood circuit from the patient following completion of plasma recovery, the time required for work performed by two persons can be drastically reduced.

Figure 2:
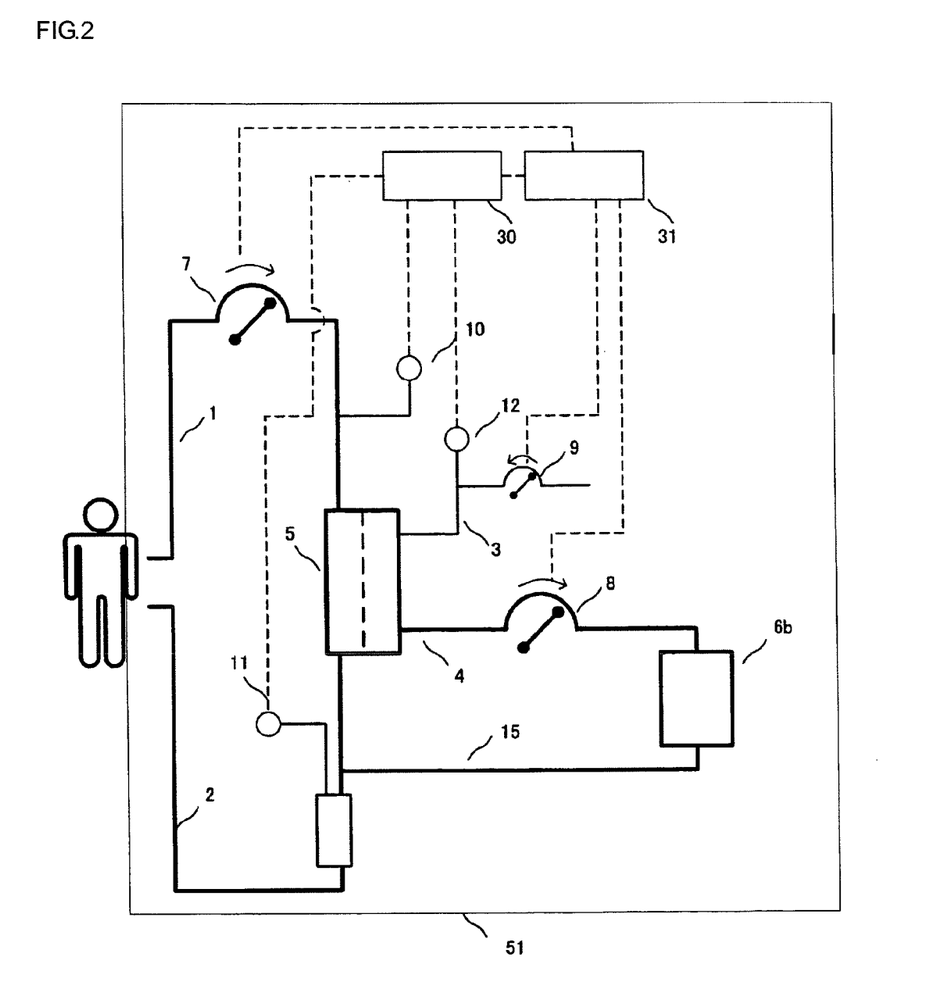
FIG. 2 is an explanatory drawing of a plasma adsorption device according to the present invention; and, FIG. 3 is an explanatory drawing of a plasma separation device of the prior art.

FIG. 2 shows an example of the configuration of a plasma adsorption device (plasma purifying device) 51 as one embodiment of the present invention.

The plasma adsorption device 51 has the plasma separator 5 and a plasma adsorber 6b. The collected blood circuit 1 is connected to a blood inlet of the plasma separator 5, and the blood pump 7 is arranged in the collected blood circuit 1. The first pressure measuring means 10 is arranged between the blood pump 7 and the plasma separator 5. The return blood circuit 2 is connected to a blood outlet of the plasma separator 5, and the second pressure measuring means 11 is arranged in the return blood circuit 2. The first pressure measurement circuit 3 is connected to a first filtration outlet of the plasma separator 5, the plasma circuit 4 is connected to a second filtration outlet, the plasma circuit 4 is connected to the plasma adsorber 6b, and the plasma pump 8 is arranged in the plasma circuit 4. The third pressure measuring means 12 and a branch line are arranged in the first pressure measurement circuit 3, and the air pump 9 is arranged in the branch line. One end of the return plasma circuit 15 is connected to an outlet of the plasma adsorber 6b, and the other end of the return plasma circuit 15 is connected to the return blood circuit 2. The plasma adsorption device 51 further has the arithmetic processing unit 30 and the control unit 31. The arithmetic processing unit 30 and the control unit 31 are connected, the arithmetic processing unit 30 is connected to the first pressure measuring means 10, the second pressure measuring means 11 and the third pressure measuring means 12, and the control unit 31 is connected to the blood pump 7, the plasma pump 8 and the air pump 9.

The above has provided a description of the overall configuration of the plasma adsorption device 51 of the present invention. Next, an explanation is provided of an operating method of the plasma adsorption device 51 that recovers blood and plasma following completion of plasma purification.

In the state in which plasma purification has been completed, the collected blood circuit 1, the return blood circuit 2 and the blood side space of the plasma separator 5 are filled with blood. In addition, the filtration side space of the plasma separator 5, the plasma circuit 4, the plasma adsorber 6b and the return plasma circuit 15 are filled with plasma. At this time, the collected blood circuit 1 and the return blood circuit 2 are still connected to the patient, and the blood pump 7 and the plasma pump 8 are still operating.

Following completion of plasma purification, plasma is first recovered. In the initial stage of plasma recovery, plasma in the filtration side space of the plasma separator 5 is recovered by delivering to the blood side space of the plasma separator 5 or to the plasma circuit 4. Plasma delivered to the blood side space is recovered in the return blood circuit 2 directly, while plasma delivered to the plasma circuit 4 is recovered in the return blood circuit 2 after passing through the plasma circuit 4, the plasma adsorber 6b and the return plasma circuit 15 as a general rule. At this time, the blood pump 7 is still operating, and blood in the collected blood circuit 1, the blood side space of the plasma separator 5 and the return blood circuit 2 is circulating. The flow rates of the air pump 9 and the plasma pump 8 are controlled so that the pressure of the filtration side space of the plasma separator 5 is higher than the pressure of the blood side space by operating the air pump 9 while still operating the plasma pump 8. More specifically, the flow rates are adjusted so that the flow rate of the air pump 9 is greater than the flow rate of the plasma pump 8. Since the flow rate of the air pump 9 is required to be greater than the flow rate of the plasma pump 8, only the air pump 9 may be operated while stopping the plasma pump 8. Since the pressure of the filtration side space of the plasma separator 5 becomes higher than the pressure of the blood side space by sending air to the filtration side space with the air pump 9, there is no additional separation of plasma from the blood in the plasma separator 5. The amount of air in the filtration side space of the plasma separator 5 gradually increases, and the filtration side space of the plasma separator 5 is ultimately replaced with air.

When air is further sent with the air pump 9 after having replaced the filtration side space of the plasma separator 5 with air, since a filtration membrane such as a hollow fiber that has been wetted has the property of not allowing the passage of air, the air that has been sent with the air pump 9 is compressed in the filtration side space of the plasma separator 5, the pressure P3 rises and the trans-membrane pressure difference TMP reaches negative pressure. At the point the trans-membrane pressure difference TMP becomes equal to or less than a certain reference value within a prescribed negative pressure range, recovery of plasma in the filtration side space of the plasma separator 5 ends. At this time, all of the plasma in the filtration side space of the plasma separator 5 is recovered into the blood side space of the plasma separator 5 or into the plasma circuit 4.

Next, plasma in the plasma circuit 4 is recovered. At this time, the blood pump 7 is still operating and blood is still circulating. In addition, plasma in the plasma circuit 4 is delivered to the plasma adsorber 6b by controlling the flow rates of the air pump 9 and the plasma pump 8 so that the trans-membrane pressure difference TMP is within a prescribed negative pressure range. As a result, since the difference in pressure between the pressure of the blood side space and the higher pressure of the filtration side space can be adjusted to be equal to or less than a preset reference value (here, an absolute value of the lower limit of the prescribed negative pressure range), an excessive load can be prevented from acting on a separation membrane of the plasma separator 5 as a result of the value of the trans-membrane pressure difference TMP being excessively low (pressure difference being excessively large) and causing a large amount of plasma in the filtration side space to attempt to flow into the blood side space. Conversely, additional plasma can be prevented from flowing into the filtration side space from the blood side space of the plasma separator 5 as a result of the trans-membrane pressure difference TMP being excessively high (pressure difference being excessively small). Furthermore, although there are no particular limitations on the negative pressure range of the trans-membrane pressure difference TMP, in consideration of measuring accuracy of the pressure measuring means and suitable internal pressure in the circuits, the prescribed negative pressure range is preferably −100 mmHg (−13.3 kPa) to −10 mmHg (−1.3 kPa). More preferably, the prescribed negative pressure range is −80 mmHg (−10.6 kPa) to −20 mmHg (−2.6 kPa).

For example, in the case the trans-membrane pressure difference TMP has become equal to or greater than the upper limit value of the prescribed negative pressure range, the flow rate of the air pump is adjusted to be greater than the flow rate of the plasma pump, while in the case the trans-membrane pressure difference TMP has become equal to or less than the lower limit value of the prescribed negative pressure range, the air pump is stopped and the plasma pump is operated. In addition, although either the flow rate of the air pump 9 or the flow rate of the plasma pump 8 may be varied provided the trans-membrane pressure difference TMP is within the prescribed negative pressure range, it is preferable to vary the flow rate of the air pump 9 while keeping the flow rate of the plasma pump 8 constant since it is preferable to maintain a constant flow rate when returning to the patient. Moreover, on/off control is preferably used to control on/off switching of the air pump 9 since this is advantageous in terms of cost.

Recovery of plasma ends once the plasma circuit 4, the plasma absorber 6b and the return plasma circuit 15 have been replaced with air. This step may be terminated while being visually confirmed by an operator, or may be terminated automatically at the time air is detected in the return plasma circuit 15 after having provided an air sensor therein.

Next, blood is recovered. At this time, the blood pump 7 is temporarily stopped, and the collected blood circuit 1 is connected to physiological saline for recovery. The duration of stoppage of the blood pump 7 is 1 minute or less, thereby eliminating the risk of coagulation of blood.

Once the collected blood circuit 1 has been connected to the physiological saline for recovery, operation of the blood pump 7 is resumed and blood is recovered from the collected blood circuit 1, the plasma separator 5 and the return blood circuit 2. Although the plasma pump 8 is stopped at this time, since recovery of plasma has already been completed, there is no risk of coagulation of the plasma.

The procedure used to recover blood and plasma and examples of the operating states of the blood pump 7, the plasma pump 8 and the air pump 9 are summarized in Table 2.

TABLE 2

| | | Ending conditions | Blood pump 7 | Plasma pump 8 | Air pump 9 |
|---|---|---|---|---|---|
| 1 | Recovery of plasma from filtration side space of plasma separator | TMP ≤ reference value within prescribed negative pressure range | ON | OFF to ON | ON Controlled so that flow rate of air pump is greater than flow rate of plasma pump |
| 2 | Recovery of plasma from plasma circuit, plasma adsorber and return plasma circuit | Visual confirmation or detection of air with air sensor | ON | ON | ON Controlled so that TMP reaches negative pressure |
| 3 | Disconnection of collected blood circuit from patient and connection of collected blood circuit to physiological saline for recovery | Visual confirmation | OFF | OFF | OFF |
| 4 | Recovery of blood from collected blood circuit, plasma separator and return blood circuit | Visual confirmation or prescribed amount of operation | ON | OFF | OFF |

As has been described above, since plasma can be recovered without stopping the blood pump 7 and recovery of plasma can be completed prior to recovery of blood, the potential for coagulation of blood and plasma can be significantly reduced. In addition, by disconnecting the collected blood circuit from the patient following completion of plasma recovery, the time required for work performed by two persons can be drastically reduced.

INDUSTRIAL APPLICABILITY

The plasma purifying device of the present invention can be used for a plasma purification method such as plasma component separation or plasma adsorption.

REFERENCE SIGNS LIST

1 Collected blood circuit
2 Return blood circuit
3 First pressure measurement circuit
4 Plasma circuit
5 Plasma separator
6a Plasma component separator
6b Plasma adsorber
7 Blood pump
8 Plasma pump
9 Air pump
10 First pressure measuring means
11 Second pressure measuring means
12 Third pressure measuring means
13 Fourth pressure measuring means
14 Branch circuit
15 Return plasma circuit
16 Return plasma pump
20 First valve
21 Second valve
30 Arithmetic processing unit
31 Control unit
50 Plasma component separation device (plasma purifying device)
51 Plasma adsorption device (plasma purifying device)

The invention claimed is:

1. A plasma purifying device, comprising:
a plasma separator for which a collected blood circuit is connected to a blood inlet, a return blood circuit is connected to a blood outlet, a first pressure measurement circuit is connected to a first filtration outlet and a plasma circuit is connected to a second filtration outlet;

a plasma component separator or plasma adsorber for which the plasma circuit is connected to a plasma inlet, and a return plasma circuit leading to the return blood circuit is connected to a plasma outlet, a blood pump which is installed in the collected blood circuit, and which supplies blood to a blood side space of the plasma separator;

a plasma pump which is installed in the plasma circuit, and which supplies plasma to the plasma component separator or the plasma adsorber;

an air pump which is installed in the first pressure measurement circuit, and which supplies air to a filtration side space of the plasma separator; and a control unit for controlling flow rates of the air pump and the plasma pump so that a pressure of the filtration side space of the plasma separator is higher than a pressure of the blood side space while delivering blood to the blood side space of the plasma separator by continuing to operate the blood pump without stopping following completion of plasma purification, and then delivering plasma remaining in the filtration side space of the plasma separator to the blood side space of the plasma separator or to the plasma circuit by supplying air from the air pump.

2. The plasma purifying device according to claim 1, wherein
the control unit delivers the plasma within the plasma circuit to the plasma component separator or the plasma adsorber by controlling the flow rates of the plasma pump and the air pump so that the difference between a pressure of the blood side space and a higher pressure of the filtration side space is not more than a preset reference value while continuing to operate the blood pump after plasma within the filtration side space of the plasma separator has been replaced with air.

3. The plasma purifying device according to claim 2, further comprising:
first pressure measuring means for measuring a pressure P1 of the collected blood circuit,
second pressure measuring means for measuring a pressure P2 of the return blood circuit,
third pressure measuring means for measuring a pressure P3 of the first pressure measurement circuit, and
an arithmetic processing unit for calculating a trans-membrane pressure difference TMP defined, from the pressures P1, P2 and P3, by either of the following formulas (1) and (2); and
the control unit delivers the plasma within the plasma circuit to the plasma component separator or the plasma adsorber by controlling the flow rates of the plasma pump and the air pump so that the trans-membrane pressure difference TMP is within a prescribed negative pressure range:

$$(P1+P2)/2-P3=TMP \tag{1}$$

$$P1-P3=TMP. \tag{2}$$

4. The plasma purifying device according to claim 3, wherein
the control unit adjusts the flow rate of the air pump so as to be greater than the flow rate of the plasma pump in a case where the trans-membrane pressure difference TMP is equal to or greater than an upper limit value of the prescribed negative pressure range, and operates the plasma pump while stopping the air pump in a case where the trans-membrane differential pressure TMP is equal to or less than the lower limit value of the prescribed negative pressure range.

5. The plasma purifying device according to claim 3, wherein the prescribed negative pressure range of the TMP is from −100 mmHg to −10 mmHg.

6. The plasma purifying device according to claim 1, wherein
the plasma purifying device has:
a plasma component separator,
fourth pressure measuring means for measuring a pressure P4 of the plasma circuit between the plasma pump and the plasma component separator,
a branch circuit connected to a first plasma component outlet of the filtration side space of the plasma component separator, and
a return plasma pump installed in the branch circuit, and
the return plasma circuit connects a second plasma component outlet of the filtration side space of the plasma component separator with the return blood circuit,
the arithmetic processing unit calculates a pressure difference ΔP defined by the following formula (3) from the pressures P3 and P4, and
the control unit delivers the plasma of the filtration side space of the plasma component separator and plasma of the return plasma circuit to the return blood circuit by stopping the plasma pump and the air pump and operating the return plasma pump while continuing to operate the blood pump when the pressure difference ΔP is equal to or greater than a reference value within a prescribed pressure range:

$$P4-P3=\Delta P \tag{3}.$$

7. The plasma purifying device according to claim 6, wherein the prescribed pressure range of the ΔP is from 200 mmHg to 500 mmHg.

8. The plasma purifying device according to claim 1, wherein
the control unit delivers the plasma of the filtration side space of the plasma separator to the blood side space of the plasma separator by operating the air pump and stopping the plasma pump.

9. A plasma purifying device, comprising:
a plasma separator for which a collected blood circuit is connected to a blood inlet, a return blood circuit is connected to a blood outlet, a first pressure measurement circuit is connected to a first filtration outlet, and a plasma circuit is connected to a second filtration outlet;
a plasma component separator or a plasma adsorber for which the plasma circuit is connected to a plasma inlet and a return plasma circuit leading to the return blood circuit is connected to a plasma outlet;
a blood pump which is installed in the collected blood circuit, and which supplies blood to a blood side space of the plasma separator;
a plasma pump which is installed in the plasma circuit, and which supplies plasma to the plasma component separator or the plasma adsorber;
an air pump which is installed in the first pressure measurement circuit, and which supplies air to a filtration side space of the plasma separator; and
a control unit for controlling flow rates of the blood pump, the plasma pump and the air pump, wherein
the control unit controls the flow rates of the air pump and the plasma pump while delivering blood to the blood side space of the plasma separator by operating the blood pump and delivers plasma remaining in the filtration side space to the blood side space and the plasma circuit by supplying air to the filtration side space of the plasma separator, and also controls the flow rates of the air pump and the plasma pump and delivers plasma remaining in the plasma circuit to the plasma component separator or the plasma adsorber.

* * * * *